United States Patent
Liu et al.

(10) Patent No.: US 6,872,869 B2
(45) Date of Patent: Mar. 29, 2005

(54) **METHOD FOR ESTABLISHING AN EXPRESSION SYSTEM OF SPIDER DRAGLINE SILK GENE IN *BOMBYX MORI***

(75) Inventors: Tianyan Liu, Chengdu (CN); Huifen Liu, Chengdu (CN); Wei Li, Chengdu (CN); Libin Zhao, Chengdu (CN)

(73) Assignee: Chengdu Tianchuang Bio-Tech Co., Ltd., Chengdu (CN)

( * ) Notice: Subject to any disclaimer, the term of this patent is extended or adjusted under 35 U.S.C. 154(b) by 240 days.

(21) Appl. No.: 09/969,852

(22) Filed: Oct. 4, 2001

(65) Prior Publication Data

US 2002/0137211 A1 Sep. 26, 2002

(30) Foreign Application Priority Data

Jan. 2, 2001 (CN) .......................................... 01106406 A (51) Int. Cl.$^7$ ........................ A61K 67/04; C12N 15/12; C12N 15/62

(52) U.S. Cl. ............................... 800/25; 800/4; 800/13; 800/21; 536/23.4

(58) Field of Search ................................. 800/4, 13, 21, 800/25; 435/320.1; 536/23.1, 23.4, 23.5

(56) References Cited

PUBLICATIONS

Sirichaisit et al. Biomacromolecules, 2003, 4: 387–394.*
Viney et al. J. Text. Inst., 2000, part 3, 2–23.*

* cited by examiner

*Primary Examiner*—Scott D. Priebe
(74) *Attorney, Agent, or Firm*—Browdy and Neimark, PLLC (57) ABSTRACT

The present invention provides a method for establishing an expression system of spider dragline silk gene in Bombyx mori. The rate of transformation is about 0.5–1%. In the silk protein produced by the transgenic Bombyx mori obtained by the method of the present invention, the spider dragline silk gene product account for 30% of the total silk proteins.

8 Claims, 10 Drawing Sheets

Fig. 4 aaatgaagcc tatatttttg gtattactcg tcgctacaag cgcctacgct gcaccatcgg tgaccatcaa
tcaatacagt gataatgaaa ttccacgcga cattgatgat ggaaaagcta gttccgtaat ctcacgtgca
tgggactacg tcgatgacac tgacaaaagc atcgccatcc tcaacgttca agagatcttg aaggacatgg
ccagccaggg cgattatgca agtcaagcat cagcggtggc ccaaaccgcc ggaattatcg cccatctatc
tgccggtatc cccggtgatg cctgtgcagc cgctaacgtc attaactctt acacagacgg cgtcaggtcc
ggaaacttcg ccggcttcag acaatctctc ggtcccttct tcggacacgt gggacaaaac ttgaatctta
tcaatcaact cgtcatcaac cctggtcaac tccgatactc tgtcggacca gccctgggtt gtgccggagg
tggaagaatc tatgacttcg aagccgcttg ggatgcaatc ttagccagca gtgactctag tttcttaaat
gaagagtact gcatcgtcaa gagattgtac aactctcgca acagccaaag caacaacatc gctgcctaca
taaccgctca cttacttcct ccggttgctc aagtgttcca ccaatcagct ggatcaatca cagacctcct
gagaggcgtt ggcaacggta atgacgcgac cggcttagtt gctaatgctc aaagatatat tgcacaagca
gccagccagg ttcacgtcta a

Fig. 5

```
gaattcaaat aacaaagtgg tgcctatccc acttttttg atccagacaa agaaaataag tgttttcggt
gagctgaaaa attaatttca ggaaacaaca aaaataatga cgcaaaagta caccggagtg aaaataaaca
ctaagaaagt aatcgctaaa aattattcat ctcgtgaatt gattgagcgc gataataacg cagtactatt
ggagagattc tatgtttaat atattaatga tatgatataa aaaagggtgc gtgtacttat gtacgcgcgt
aagaagttat actttatttt cattaaattt atttcttttt ttttatttca attttaatca
atttgaaaaa aaatcgaata aacaacatcc tcaaacatgc atattggaca tcccttttct tgacatcgta
taaattcggt aattctcggt acggttcgta aagttcacct gcggctatat tccgactcgc caagttacgt
cagtcgtatt gtaatgagcg atttagtggg caacttcatt ctgttaattt tgtgtcacgg tgcgcgcgca
tcgtaaaact tcactctcat agattttca taacgcgcct aaagaagtat aacttcaata atttaaattt
aaaaaaaaac atgcatagaa taattatatg aattatttaa aatgtcattt accgacattg acataacaga
cgacgttaac actacaaaac attttaattc cacattgtta catattcaac agttaaattt gcgttaattc
tcgatgcgaa caaatataag aacaatcgga tcaattagat cgctttgttt cgaacaacac ttagtttaac
tagaggcgta caccctcaaga aatcatcttc attagaaact aaaccttaaa atcgcaataa taaagcatag
tcaattttaa ctgaaatgca aagtcttttg aacgttagat gctgtcagcg ttcgttggta cagttgtttg
atatttattt taattgtctt tttatatata aatagtggaa cattaatcac ggaatcctgt atagtatata
ccgattggtc acataacaga ccactaaa
```

Fig. 6

```
taaataa gaactgtaaa taatgtatat atataattat ataaaagata tatataacca tatacaaaca
tatatatcat tataagacaa tctacctata taaaaacaga ctaaaattaa taattatgta tactttaatt
gtgtttagga cattttatgc aaattgtgtt tgcgttagga ttttttttgg aagtttttta gattatttat
gaatatataa ataaatatac gttaatataa tatatattat ataaatcaac gacacggctt ttcattttgg
tgatgatcaa tcttattgtt cttctaattg attttttttgt acaataaaga tgtatccagt tttccagata
aagaatttag tttgttattt ctggccccat taaaataagt acggtattcg acaataccac atagtatata
cccaaagacg gtggattgga cagtgggtac atggatttcg gtactgttgt catgct
```

Fig. 7

```
gcagcagcag cagctggagg tgccggacaa ggaggatatg gaggtcttgg
aagccagggt gctggacgag gtggacaagg tgcaggcgca gccgcagccg
cagctggagg tgctggtcaa ggaggatacg gaggtcttgg aagccaaggt
gctggacgag gaggattagg tggacaaggt gcaggtgcag cagcagcagc
agcagctgga ggtgtcggac aaggaggact aggtggacaa ggtgctggac
aaggagctgg agcagccgct gcagcagctg gtggtgccgg acaaggagga
tatggaggtc tcggaagcca aggtgcagga cgaggtggat caggtggaca
aggggcaggt gcagcagcag cagcagctgg aggtgccgga caaggaggat
atggaggtct tggaagccaa ggtgcaggac gaggtggatt aggtggacaa
ggtgcaggtg cagcagcagc agcagcagcc ggaggtgctg gacaaggagg
atacggtggt cttggtggac aaggtgccgg acaaggtggc tatggaggac
ttggaagcca aggtgccgga cgaggaggat taggtggaca aggtgcaggt
gcagcagcag cagcagcagc tggaggtgcc ggacaaggag gactaggtgg
acaaggtgct ggacaaggag ctggagcagc cgctgcagca gctggtggtg
ccggacaagg aggatatgga ggtcttggaa gccaaggtgc tggacgaggt
ggacaaggtg caggcgcagc cgcagcagca gccgtaggtg ctggacaagg
aggatacggt ggacaaggtg ccggacaagg aggctatgga ggacttggaa
gtcaaggtgc tggacgagga ggattaggtg gacaaggtgc aggtgcagca
gcagcagcag cagctggagg tgccggacag ggaggattag gtggacaagg
tgctggacaa ggagctggag cagccgctgc agcagctggt ggtgccggac
aaggaggata tggaggtctt ggaaaccaag gtgctggacg aggtggacaa
ggtgcagcag cagcagcagc tggaggtgct ggacaaggag gatatggagg
tcttggaagc caaggtgcag gacgaggtgg attaggtgga caaggtgcag
gtgcagcagc agcagcagct ggaggtgctg gacaaggagg atacggtggt
cttggtggac aaggtgccgg acaaggaggc tatggaggac ttggaagcca
aggttctggt cgaggaggat taggtggaca aggtgcaggt gcagcagcag
cagcagctgg aggtgctgga caaggaggat taggtggaca aggtgctgga
caaggagctg gagcagccgc tgcagcagct ggtggtgtta gacaaggagg
atatggaggt cttggaagcc aaggtgctgg acgaggtgga caaggtgcag
gcgcagccgc agcagcagcc ggaggtgctg gacaaggagg atatggtggt
cttggtggac aaggtgttgg ccgaggtgga ttaggtggac aaggtgcagg
cgcagcggca gctggtggtg ctggacaagg aggatatggt ggtgttggtt
ctggggcgtc tgctgcctct gcagctgcat cccgtttgtc ttctcctcaa
gctagttcaa gagtttcatc agctgtttcc aacttggttg caagtggtcc
tactaattct gcggccttgt caagtacaat cagtaacgtg gtttcacaaa
taggcgccag caatcctggt ctttctggat gtgatgtcct cattcaagct
cttctcgagg ttgtttctgc tcttatccag atcttaggtt cttccagcat
cg
```

Fig. 8

```
tcaaaagatg cgagctgata gcgtgcgcgt taccatatat ggtgacaaaa actgagtcag cccgcgattg
gtggaaaaac aaactggagc cgatactgtg taaattgtga taacggctct tttatatagt ttatcctcac
gagtcggttc tcatttacta aggtgtgctc gaacagtgcg cattcgcatc tacgtacttg tcacttattt
aataatacta tgtaagtttt aattttaaaa ttgcgaaaga aaaaaaaaca tatttattta tttgtaaaat
ttgaatttcg aaggttctcc gtccctttac ctttaagtat tacatatgtt tgagtgtttt ttttttttaa
taatacgcta atgataacgt gttacgttac ataattgttg cataactagt gaagtgaaat tttttataaa
aaaaaacatt tttcggaatt tagtgtactg cagatgttaa taaacactac taaataagaa ataagtttat
tggacgcaca tttcaaagtg tccactcgca tcgatcaatt cggaaacaga aattggggaac agtgaattat
gaatcttata cagttttctt taacgtcact aaatagatgg acgcaaataa atttgtcgtt tacttagtat
aatgtatgga atgagaatgt agtttgaatt gtttttttc ttttcttgca gactaattca agatgtgcga
cgaagaagtt
```

Fig. 9

```
atgggatg ttctttagac gatgagcata tcctctctgc tcttctgcaa ggcgatgacg agcttgttgg
tgaggattct gacagtgaaa tatcagatca cgtaagtgaa gacgtccaga gcgatacaga agaagcgttt
atagatgagg tacatgaagt gtcagccaac gtcaagcgta gtgaaatatt agacgaacaa aatgttattg
aacaaccagg ttcttcattg gcttctaaca gaatcttgac cttgccacag aggactatta gaggtaagaa
taaacattgt tggtcaactt caaagtccac gagcggtagc cgagtctctg cactgaacat tgtcagatct
caaagaggtc cgacgcgtat gtgccgcaat atatatgacc cactttatg cttcaaacta tttttactg
atgagataat ttcgcaaatt gtaaaatgga caaatgctga gatatcattg aaacgtcggg aatctatgac
aggtgctaca tttcgtgaca cgaatgaaga tgaaatctat gctttctttg gtattctggt aatgacagca
gtgagaaaag ataaccacat gtccacagat gacctctttg gatcgatctt tgtcaatgtg tacgtctctg
taatgagtct gtggatcgtt ttggattttt tgatacgatg tcttagaatg gatgacaaaa gtatacggcc
cacacttcga gaaaacgatg tatttactcc tgttagaaaa atatgggatc tctttatcca tcagtgcata
caaaattaca ctccaggggc tcatttgacc atagatgaac agttacttgg ttttagagga cggtgtccgt
ttaggatgta tatcccaaac aagccaagta agtatggaat aaaatcctca tgatgtgtga cagtggtacg
aagtatatga taaatggaat gccttatttg ggaagaggaa cacagaccaa cggagtacca ctcggtgaat
actacgtgaa ggagttatca aagcctgtgc acggtagttg tcgtaatatt acgtgtgaca attggttcac
ctcaatccct ttggcaaaaa acttactaca agaaccgtat aagttaacca ttgtgggaac cgtgcgatca
aacaaacgcg agataccgga agtactgaaa acagtcgct ccaggccagt gggaacatcg atgttttgtt
ttgacggacc ccttactctc gtctcatata aaccgaagcc agctaagatg gtatacttat tatcatcttg
tgatgaggat gcttctatca acgaaagtac cggtaaaccg caaatggtta tgtattataa tcaaactaaa
ggcggagtgg acacgctaga ccaaatgtgt tctgtgatga cctgcagtag gaagacgaat aggtggccta
tggcattatt gtacggaatg ataaacattg cctgcataaa ttcttttatt atatacagcc ataatgtcag
tagcaaggga gaaaaggttc aaagtcgcaa aaaattatg agaaaccttt acatgagcct gacgtcatcg
tttatgcgta accgtttaga agctcctact ttgaagagat atttgcgcga taatatctct aatatttgc
caaatgaagt gcctggtaca tcagatgaca gtactgaaga gccagtaatg aaaaaacgta cttactgtac
ttactgcccc tctaaaataa ggcgaaaggc aaatgcatcg tgcaaaaaat gcaaaaaagt tatttgtcga
gagcataata ttgatatgtg ccaaagttgt ttctggactg actaataagt ataatttgtt tctattatgt
ataagttaag ctaattactt attttataat acaacatgac tgtttttaaa gtacaaaata agtttatttt
tgtaaaagag agaatgttta aaagttttgt tactttagaa gaaattttga gtttttgttt tttttaata
aataaataaa cataaataaa ttgtttgttg aatttattat tagtatgtaa gtgtaaatat aataaaactt
aatatctatt caaattaata aataaacctc gatatacaga ccgataaaaa
```

Fig. 10

SEQUENCE LISTING

<160> NUMBER OF SEQ ID NOS: 14

<210> SEQ ID NO 1
<211> LENGTH: 791
<212> TYPE: DNA
<213> ORGANISM: Bombyx mori

<400> SEQUENCE: 1

```
aaatgaagcc tatatttttg gtattactcg tcgctacaag cgcctacgct gcaccatcgg      60
tgaccatcaa tcaatacagt gataatgaaa ttccacgcga cattgatgat ggaaaagcta     120
gttccgtaat ctcacgtgca tgggactacg tcgatgacac tgacaaaagc atcgccatcc     180
tcaacgttca agagatcttg aaggacatgg ccagccaggg cgattatgca agtcaagcat     240
cagcggtggc ccaaaccgcc ggaattatcg cccatctatc tgccggtatc cccggtgatg     300
cctgtgcagc cgctaacgtc attaactctt acacagacgg cgtcaggtcc ggaaacttcg     360
ccggcttcag acaatctctc ggtcccttct tcggacacgt gggacaaaac ttgaatctta     420
tcaatcaact cgtcatcaac cctggtcaac tccgatactc tgtcggacca gccctgggtt     480
gtgccggagg tggaagaatc tatgacttcg aagccgcttg ggatgcaatc ttagccagca     540
gtgactctag tttcttaaat gaagagtact gcatcgtcaa gagattgtac aactctcgca     600
acagccaaag caacaacatc gctgcctaca taaccgctca cttacttcct ccggttgctc     660
aagtgttcca ccaatcagct ggatcaatca cagacctcct gagaggcgtt ggcaacggta     720
atgacgcgac cggcttagtt gctaatgctc aaagatatat tgcacaagca gccagccagg     780
ttcacgtcta a                                                          791
```

<210> SEQ ID NO 2
<211> LENGTH: 1068
<212> TYPE: DNA
<213> ORGANISM: Bombyx mori

<400> SEQUENCE: 2

```
gaattcaaat aacaaagtgg tgcctatccc actttttttg atccagacaa agaaaataag      60
tgttttcggt gagctgaaaa attaatttca ggaaacaaca aaaataatga cgcaaaagta     120
caccggagtg aaaataaaca ctaagaaagt aatcgctaaa aattattcat ctcgtgaatt     180
gattgagcgc gataataacg cagtactatt ggagagattc tatgtttaat atattaatga     240
tatgatataa aaagggtgc gtgtacttat gtacgcgcgt aagaagttat actttattt      300 cattaaattt atttcttttt ttttatttca attttaatca atttgaaaaa aaatcgaata     360
```

-continued

```
aacaacatcc tcaaacatgc atattggaca tcccttttct tgacatcgta taaattcggt    420
aattctcggt acggttcgta aagttcacct gcggctatat tccgactcgc caagttacgt    480
cagtcgtatt gtaatgagcg atttagtggg caacttcatt ctgttaattt tgtgtcacgg    540
tgcgcgcgca tcgtaaaact tcactctcat agattttca taacgcgcct aaagaagtat     600
aacttcaata atttaaattt aaaaaaaaac atgcatagaa taattatatg aattatttaa    660
aatgtcattt accgacattg ataacagac cgacgttaac actacaaaac atttaattc       720 cacattgtta catattcaac agttaaattt gcgttaattc tcgatgcgaa caaatataag    780
aacaatcgga tcaattagat cgctttgttt cgaacaacac ttagtttaac tagaggcgta    840
cacctcaaga aatcatcttc attagaaact aaaccttaaa atcgcaataa taaagcatag     900
tcaattttaa ctgaaatgca aagtcttttg aacgttagat gctgtcagcg ttcgttggta    960
cagttgtttg atatttattt taattgtctt tttatatata aatagtggaa cattaatcac    1020
ggaatcctgt atagtatata ccgattggtc acataacaga ccactaaa                 1068

<210> SEQ ID NO 3
<211> LENGTH: 473
<212> TYPE: DNA
<213> ORGANISM: Bombyx mori

<400> SEQUENCE: 3
taaataagaa ctgtaaataa tgtatatata taattatata aagatatat ataaccatat      60 acaaacatat atatcattat aagacaatct acctatataa aaacagacta aaattaataa    120
ttatgtatac tttaattgtg tttaggacat tttatgcaaa ttgtgtttgc gttaggattt    180 ttttttggaag ttttttagat tatttatgaa tatataaata aatatacgtt aatataaat    240 atattatata aatcaacgac acggcttttc attttggtga tgatcaatct tattgttctt    300
ctaattgatt tttttgtaca ataaagatgt atccagtttt ccagataaag aatttagttt    360
gttatttctg gccccattaa aataagtacg gtattcgaca ataccacata gtatataccc    420
aaagacggtg gattggacag tgggtacatg gatttcggta ctgttgtcat gct           473

<210> SEQ ID NO 4
<211> LENGTH: 1852
<212> TYPE: DNA
<213> ORGANISM: Nephila clavipes

<400> SEQUENCE: 4
gcagcagcag cagctggagg tgccggacaa ggaggatatg gaggtcttgg aagccagggt     60
gctggacgag gtggacaagg tgcaggcgca gccgcagccg cagctggagg tgctggtcaa    120
ggaggatacg gaggtcttgg aagccaaggt gctggacgag gaggattagg tggacaaggt    180
gcaggtgcag cagcagcagc agcagctgga ggtgtcggac aaggaggact aggtggacaa    240
ggtgctggac aaggagctgg agcagccgct gcagcagctg tggtgccgg acaaggagga    300 tatggaggtc tcggaagcca aggtgcagga cgaggtggat caggtggaca aggggcaggt    360
gcagcagcag cagcagctgg aggtgccgga caaggaggat atggaggtct tggaagccaa    420
ggtgcaggac gaggtggatt aggtggacaa ggtgcaggtg cagcagcagc agcagcagcc    480
ggaggtgctg gacaaggagg atacggtggt cttggtggac aaggtgccgg acaaggtggc    540
tatggaggac ttgaagcca aggtgccgga cgaggaggat taggtggaca aggtgcaggt    600
gcagcagcag cagcagcagc tggaggtgcc ggacaaggag gactaggtgg acaaggtgct    660
ggacaaggag ctggagcagc cgctgcagca gctggtggtg ccggacaagg aggatatgga    720
```

-continued

| | |
|---|---|
| ggtcttggaa gccaaggtgc tggacgaggt ggacaaggtg caggcgcagc cgcagcagca | 780 |
| gccgtaggtg ctggacaagg aggatacggt ggacaaggtg ccggacaagg aggctatgga | 840 |
| ggacttggaa gtcaaggtgc tggacgagga ggattaggtg acaaggtgc aggtgcagca | 900 |
| gcagcagcag cagctggagg tgccggacag ggaggattag gtggacaagg tgctggacaa | 960 |
| ggagctggag cagccgctgc agcagctggt ggtgccggac aaggaggata tggaggtctt | 1020 |
| ggaaaccaag gtgctggacg aggtggacaa ggtgcagcag cagcagcagc tggaggtgct | 1080 |
| ggacaaggag gatatggagg tcttggaagc caaggtgcag gacgaggtgg attaggtgga | 1140 |
| caaggtgcag gtgcagcagc agcagcagct ggaggtgctg acaaggagg atacggtggt | 1200 |
| cttggtggac aaggtgccgg acaaggaggc tatggaggac ttggaagcca aggttctggt | 1260 |
| cgaggaggat taggtggaca aggtgcaggt gcagcagcag cagcagctgg aggtgctgga | 1320 |
| caaggaggat taggtggaca aggtgctgga caaggagctg agcagccgc tgcagcagct | 1380 |
| ggtggtgtta gacaaggagg atatggaggt cttggaagcc aaggtgctgg acgaggtgga | 1440 |
| caaggtgcag gcgcagccgc agcagcagcc ggaggtgctg acaaggagg atatggtggt | 1500 |
| cttggtggac aaggtgttgg ccgaggtgga ttaggtggac aaggtgcagg cgcagcggca | 1560 |
| gctggtggtg ctggacaagg aggatatggt ggtgttggtt ctggggcgtc tgctgcctct | 1620 |
| gcagctgcat cccgtttgtc ttctcctcaa gctagttcaa gagtttcatc agctgtttcc | 1680 |
| aacttggttg caagtggtcc tactaattct gcggccttgt caagtacaat cagtaacgtg | 1740 |
| gtttcacaaa taggcgccag caatcctggt cttctggat gtgatgtcct cattcaagct | 1800 |
| cttctcgagg ttgtttctgc tcttatccag atcttaggtt cttccagcat cg | 1852 |

<210> SEQ ID NO 5
<211> LENGTH: 710
<212> TYPE: DNA
<213> ORGANISM: Bombyx mori

<400> SEQUENCE: 5

| | |
|---|---|
| tcaaagatg cgagctgata gcgtgcgcgt taccatatat ggtgacaaaa actgagtcag | 60 |
| cccgcgattg gtgaaaaac aaactggagc cgatactgtg taaattgtga taacggctct | 120 |
| tttatatagt ttatcctcac gagtcggttc tcatttacta aggtgtgctc gaacagtgcg | 180 |
| cattcgcatc tacgtacttg tcacttattt aataatacta tgtaagtttt aatttaaaa | 240 |
| ttgcgaaaga aaaaaaaca tatttattta tttgtaaaat ttgaatttcg aaggttctcc | 300 |
| gtcccttac ctttaagtat tacatatgtt tgagtgtttt tttttttaa taatacgcta | 360 |
| atgataacgt gttacgttac ataattgttg cataactagt gaagtgaaat tttttataaa | 420 |
| aaaaaacatt tttcggaatt tagtgtactg cagatgttaa taaacactac taaataagaa | 480 |
| ataagtttat tggacgcaca tttcaaagtg tccactcgca tcgatcaatt cggaaacaga | 540 |
| aattgggaac agtgaattat gaatcttata cagttttctt taacgtcact aaatagatgg | 600 |
| acgcaaataa atttgtcgtt tacttagtat aatgtatgga atgagaatgt agtttgaatt | 660 |
| gttttttttc ttttcttgca gactaattca agatgtgcga cgaagaagtt | 710 |

<210> SEQ ID NO 6
<211> LENGTH: 2078
<212> TYPE: DNA
<213> ORGANISM: Trichoplusia ni

<400> SEQUENCE: 6

-continued

| | |
|---|---|
| atgggatgtt ctttagacga tgagcatatc ctctctgctc ttctgcaagg cgatgacgag | 60 |
| cttgttggtg aggattctga cagtgaaata tcagatcacg taagtgaaga cgtccagagc | 120 |
| gatacagaag aagcgtttat agatgaggta catgaagtgt cagccaacgt caagcgtagt | 180 |
| gaaatattag acgaacaaaa tgttattgaa caaccaggtt cttcattggc ttctaacaga | 240 |
| atcttgacct tgccacagag gactattaga ggtaagaata acattgttg gtcaacttca | 300 |
| aagtccacga gcggtagccg agtctctgca ctgaacattg tcagatctca aagaggtccg | 360 |
| acgcgtatgt gccgcaatat atatgaccca cttttatgct tcaaactatt ttttactgat | 420 |
| gagataattt cgcaaattgt aaaatggaca atgctgaga tatcattgaa acgtcgggaa | 480 |
| tctatgacag gtgctacatt tcgtgacacg aatgaagatg aaatctatgc tttctttggt | 540 |
| attctggtaa tgacagcagt gagaaaagat aaccacatgt ccacagatga cctctttgga | 600 |
| tcgatctttg tcaatgtgta cgtctctgta atgagtctgt ggatcgtttt ggattttttg | 660 |
| atacgatgtc ttagaatgga tgacaaaagt atacggccca cacttcgaga aaacgatgta | 720 |
| tttactcctg ttagaaaaat atgggatctc tttatccatc agtgcataca aaattacact | 780 |
| ccagggctc atttgaccat agatgaacag ttacttggtt ttagaggacg gtgtccgttt | 840 |
| aggatgtata tcccaaacaa gccaagtaag tatggaataa aatcctcatg atgtgtgaca | 900 |
| gtggtacgaa gtatatgata atggaatgc cttatttggg aagaggaaca cagaccaacg | 960 |
| gagtaccact cggtgaatac tacgtgaagg agttatcaaa gcctgtgcac ggtagttgtc | 1020 |
| gtaatattac gtgtgacaat tggttcacct caatcccttt ggcaaaaaac ttactacaag | 1080 |
| aaccgtataa gttaaccatt gtgggaaccg tgcgatcaaa caaacgcgag ataccggaag | 1140 |
| tactgaaaaa cagtcgctcc aggccagtgg gaacatcgat gttttgtttt gacggacccc | 1200 |
| ttactctcgt ctcatataaa ccgaagccag ctaagatggt atacttatta tcatcttgtg | 1260 |
| atgaggatgc ttctatcaac gaaagtaccg gtaaaccgca aatggttatg tattataatc | 1320 |
| aaactaaagg cggagtggac acgctagacc aaatgtgttc tgtgatgacc tgcagtagga | 1380 |
| agacgaatag gtggcctatg gcattattgt acggaatgat aaacattgcc tgcataaatt | 1440 |
| ctttattat atacagccat aatgtcagta gcaagggaga aaaggttcaa agtcgcaaaa | 1500 |
| aatttatgag aaacctttac atgagcctga cgtcatcgtt tatgcgtaac cgtttagaag | 1560 |
| ctcctacttt gaagagatat ttgcgcgata atatctctaa tattttgcca aatgaagtgc | 1620 |
| ctggtacatc agatgacagt actgaagagc cagtaatgaa aaaacgtact tactgtactt | 1680 |
| actgcccctc taaaataagg cgaaaggcaa atgcatcgtg caaaaaatgc aaaaaagtta | 1740 |
| tttgtcgaga gcataatatt gatatgtgcc aaagttgttt ctggactgac taataagtat | 1800 |
| aatttgtttc tattatgtat aagttaagct aattacttat tttataatac aacatgactg | 1860 |
| tttttaaagt acaaaataag tttatttttg taaaagagag aatgtttaaa agttttgtta | 1920 |
| ctttagaaga aattttgagt ttttgttttt tttaataaa taaataaaca taaataaatt | 1980 |
| gtttgttgaa tttattatta gtatgtaagt gtaaatataa taaaacttaa tatctattca | 2040 |
| aattaataaa taaacctcga tatacagacc gataaaaa | 2078 |

<210> SEQ ID NO 7
<211> LENGTH: 22
<212> TYPE: DNA
<213> ORGANISM: Artificial Sequence
<220> FEATURE:
<223> OTHER INFORMATION: primer

<400> SEQUENCE: 7

```
acggatccaa atgaagccta ta                                              22

<210> SEQ ID NO 8
<211> LENGTH: 24
<212> TYPE: DNA
<213> ORGANISM: Artificial Sequence
<220> FEATURE:
<223> OTHER INFORMATION: primer

<400> SEQUENCE: 8
ggctgcagtt agacgtgaac ctgg                                            24

<210> SEQ ID NO 9
<211> LENGTH: 29
<212> TYPE: DNA
<213> ORGANISM: Artificial Sequence
<220> FEATURE:
<223> OTHER INFORMATION: Primer

<400> SEQUENCE: 9
gagctcgaat tcaaataaca aagtggtgc                                       29

<210> SEQ ID NO 10
<211> LENGTH: 23
<212> TYPE: DNA
<213> ORGANISM: Artificial Sequence
<220> FEATURE:
<223> OTHER INFORMATION: Primer

<400> SEQUENCE: 10
ctctagatta gtggtctgtt atg                                             23

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
gcagcagcag cagctggagg                                                 20

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
cgatgctgga agaacctaag                                                 20

<210> SEQ ID NO 13
<211> LENGTH: 30
<212> TYPE: DNA
<213> ORGANISM: Artificial Sequence
<220> FEATURE:
<223> OTHER INFORMATION: MCS

<400> SEQUENCE: 13
accgcggtct agaggatccc gggctgcagt                                      30

<210> SEQ ID NO 14
<211> LENGTH: 51
<212> TYPE: DNA
```

-continued

```
<213> ORGANISM: Trichoplusia ni

<400> SEQUENCE: 14
cgccgcggcc ctagaaagat agtctgcgta aaattgacgc atgctgcagt g          51
```

METHOD FOR ESTABLISHING AN EXPRESSION SYSTEM OF SPIDER DRAGLINE SILK GENE IN BOMBYX MORI

FIELD OF THE INVENTION

The present invention relates to a method for establishing an expression system of spider dragline silk gene in *Bombyx mori*.

BACKGROUND OF THE INVENTION

Spider silk is a natural fiber with special physical and chemical characteristics. It has excellent tensile strength, elasticity and is resistant to mold. Spider silk gene has been demonstrated to be expressed in *Escherichia coli* or yeast, however, products with the mechanic characteristics of the natural fibre failed to be obtained, because the process and mechanism by which the natural silk fibre is formed from protein is still unknown. *Bombyx mori* has been used as a bio-reactor to commercially produce a number of polypeptides or proteins. However, the potentiality of *Bombyx mori* to be used as the host of expression of interesting products is very much limited for the following reasons: (1) the transgenic system of *Bombyx mori* is unstable and the integrated extraneous DNAs are of transient expression; (2) the mechanisms of synthesis, processing, transporting, and secretion of the silk fibroin is unknown. As a result, the application of *Bombyx mori* as the host for expressing foreign proteins is limited.

DISCLOSURE OF THE INVENTION

It is an object of the present invention to provide a method for establishing an expression system of spider dragline silk gene in *Bombyx mori*.

The present invention thus provides a method for establishing an expression system of spider dragline silk gene in *Bombyx mori*, comprising the steps of:
(1) ligating the cDNA encoding spider dragline silk protein or the cDNA encoding the part of repetitive amino acid of the protein with the cDNA encoding L chain of silk protein, placing the ligated DNA under the control of the promoter of the L chain gene and terminating the ligated DNA with the terminator of the L chain gene, thereby obtaining a fused gene;
(2) ligating the fused gene with a reporter gene, inserting the ligated product thus obtained between the two inverted terminal repeats of the transposon of piggyBac, thereby obtaining a recombinant transposon;
(3) constructing a transposase gene expression vector by using the transposase gene;
(4) co-transforming a silkworm egg by using the recombinant transposon obtained in step (2) and the transposase gene expression vector obtained in step (3);
(5) obtaining a transgenic silkworm which expresses the exogenous spider dragline silk protein by cultivating and screening the larva of the transformed eggs in step (4).

Spider dragline is a major ampullate silk with excellent tensile strength and elasticity. Dragline is used as a strong yet flexible structural element in the web, and as a belaying line for spider to climb (Gosline J. M. et al.,1986, Endeavour 10,37–43). Silkworm silk is another important natural protein fiber, which is mainly composed of light(L)-chain and heavy(H)-chain. L and H-chain are linked by a disulfide bond to form the unit of silk fibroin, and the L-chain is essential for the secretion of the fibroin. Corresponding to the repetitive amino acid sequence, the cDNA of dragline has repetitive nucleotide sequences. The cDNA of dragline can be cloned by screening the cDNA library of spider major ampullate gland, using the DNA fragment corresponding to the repetitive amino acid sequence as a probe (Gosline J. M. et al.,1999, J. Exp. Biol. 302, 3295–3303).

The spider dragline expression unit must be constructed correctly for its expression, secretion, regulation and the formation of the protein fiber. In this invention, the L-chain cDNA and the promoter thereof was fused upstream of the dragline gene cDNA to direct the expression and secretion of the dragline protein.

The expression of the fibroin gene of *Bombyx mori* was regulated by a number of factors, some of which is still unknown. In this invention the promoter of L-chain was used to promote the transcription of the L chain-dragline fusion, wherein the 5' end of the spider dragline silk gene cDNA or the part of the repetitive nucleotide sequence was fused to the 3' terminal of the L chain cDNA to form a fusion with correct reading frame. Then the fusion was placed under the control of the promoter and terminator of the L chain to form a complete "L chain-dragline" recombinant gene expression unit. Accordingly, the expression of this fusion gene in *Bombyx mori* is under the control of the L chain promoter, and the presence of L chain protein assured the correct secretion of the fusion gene product and the formation of the protein fiber. The promoter and terminator of L chain can be cloned by PCR from the genome of *Bombyx mori*, and the L chain cDNA can be cloned and amplified by RT-PCR from the total RNA or mRNA of the post silk gland (PSG) of the larvae of fifth instar(Yamaguchi K et al., 1989, J Mol Bio 22:55–67).

The green fluorescence protein(GFP), which was found in the multichannel jellyfish in the Arctic, can be expressed in many species, such as bacteria, slime mold, plant, and animal, under the direction of appropriate promoters. GFP, which is often used as an expression reporter, can be irritated by UV without the presence of any cofactors, and can be detected conveniently with high sensitivity in vivo. In this invention, the GFP gene was placed downstream of the silkworm A3promoter of cytoplasmical actin gene, and was used as a reporter of the transformation of *Bombyx mori*.

In order to facilitate the transferring of the "L chain-dragline" fusion gene into the *Bombyx mori* genome, a gene transformation system derived from piggyBac transposon was constructed. The piggyBac transposon of Trichoplusia ni has a size of 2.0 Kb. It has shown that the transposition of piggyBac occurred in many species of *Diptera* and *Lepidoptera*. The two inverted terminal repeats(ITR) flank two reading frames, one of which codes for the transposase. When transposition occurred, the transposase recognized the ITRs, and promotes the transposition of the sequence flanked by the two ITRs. In this invention, the piggyBac transposon was changed into a gene-delivering vector by DNA recombination techniques: the "L chain-dragline" fusion gene and GFP reporter were ligated by a artificial linker, and the product replaces the sequence flanked by the two ITRs on the piggyBac. This gene-delivering vector can efficiently transform and integrate the target gene into *Bombyx mori* genome.

Transposase is another essential factor for the transposition to take place. It recognizes the ITRs, and initiates the transposition. In this invention, the transposase was cloned into a vector which is different from the piggyBac-derived gene-delivering vector, and which is called helper vector. The A3 promoter was used to direct the expression of the transposase in the helper vector. When the helper vector and the piggyBac-derived gene-delivering vector were co-transformed into the silkworm eggs, the transiently expressed transposase in the helper vector initiated the transposition to take place.

By using the two-vector system, a helper vector expressing transposase and a piggyBac-derived gene-delivering vector which contains the fusion gene to be integrated into the *Bombyx mori* genome, the fusion gene can be integrated into the *Bombyx mori* genomic DNA efficiently, and also have genetic stability after the integration takes place.

After the construction of the helper vector which expresses transposase and the piggyBac-derived gene-delivering vector which contains the fusion gene to be integrated into the *Bombyx mori* genome, the two vectors are simultaneously microinjected into the *Bombyx mori* eggs. And the transformed eggs are allowed to developed under conditions known in the art.

The GFP of silkworm of the fifth instar are tested under UV of 390 nm wavelength, and the individuals with positive result in the test are labeled. The dragline protein content of the cocoons of these GFP-positive individuals is measured later, and the dragline protein positive individuals are also labeled. Then the dragline protein positive individuals are crossbred, and the offspring are screened to obtain transgenic silkworm which can stably express dragline protein. The transgenic silkworms thus obtained have DNA sequence encoding the spider dragline protein, and thus can synthesize and secrete dragline protein-containing silk when they cocoon. This kind of dragline protein-containing silk has significantly higher mechanic strength and elasticity than normal silk.

Briefly speaking, this invention provides a method of constructing a constitutive transgeneic system, which makes extraneous gene integrate into the genomic DNA with high efficiency and with several copies. The frequency of transformation is about 0.5–1%. The result of analysis of the product produced by the transgenic *Bombyx mori* showed that the fused spider dragline silk gene product account for 30% of the total silk proteins.

BRIEF DESCRIPTION OF THE DRAWINGS

FIG. 8 shows the part of repetitive nucleotide sequence (SEQ ID NO:4) of the cDNA of spider dragline;

EXAMPLES

The invention will be illustrated in further detail with the following Examples.

Figure 1:
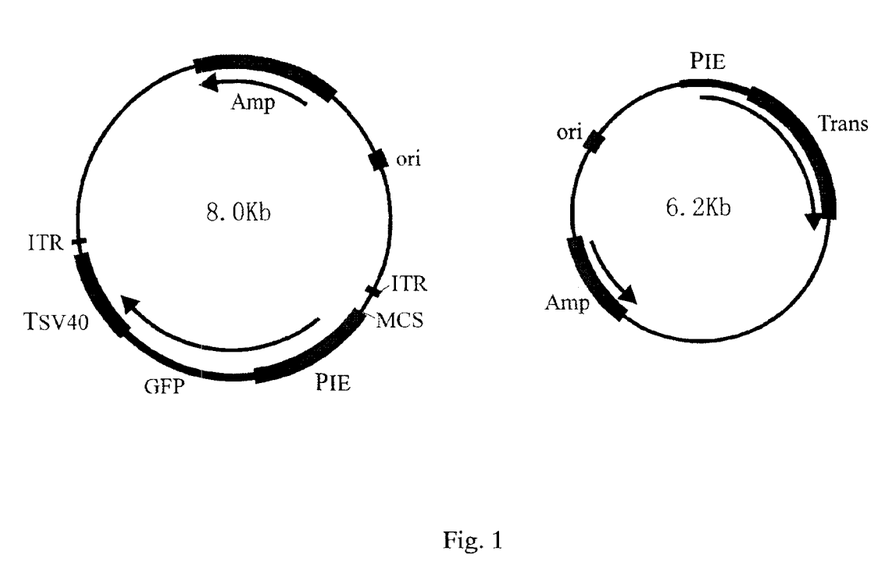
FIG. 1 schematically shows the piggyBac transposon derived gene-delivering vector and the transposase-expressing helper vector.
Figure 2:
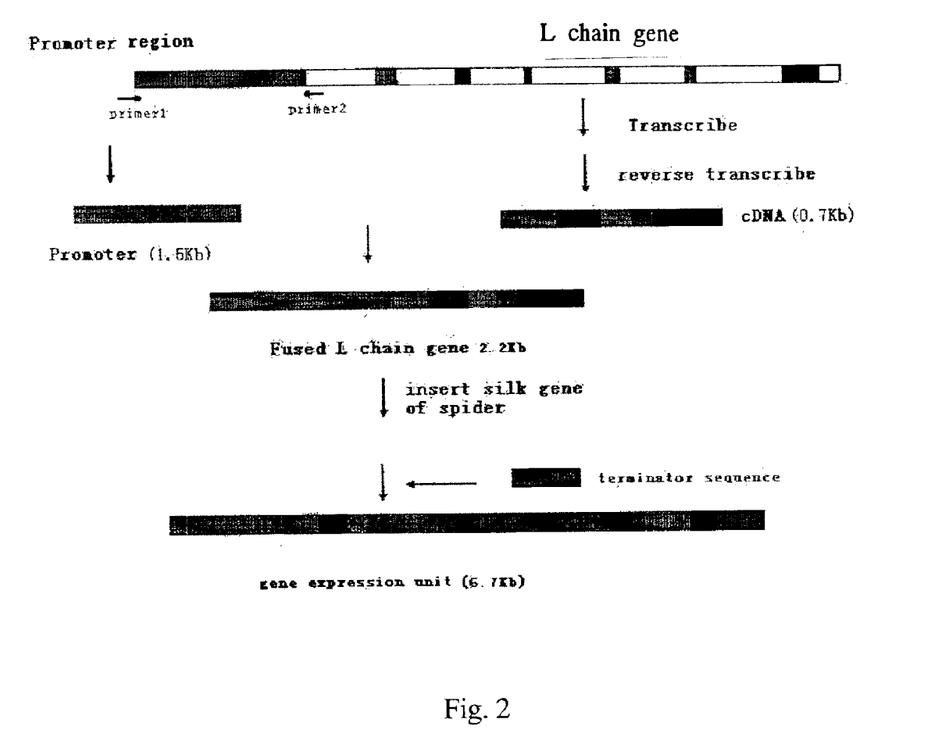
FIG. 2 shows the construction of the "L chain-dragline" fusion gene.

Example 1
Construction of the Expression Unit of L Chain-dragline Fusion Gene(shown in FIG. 2)

Figure 5:
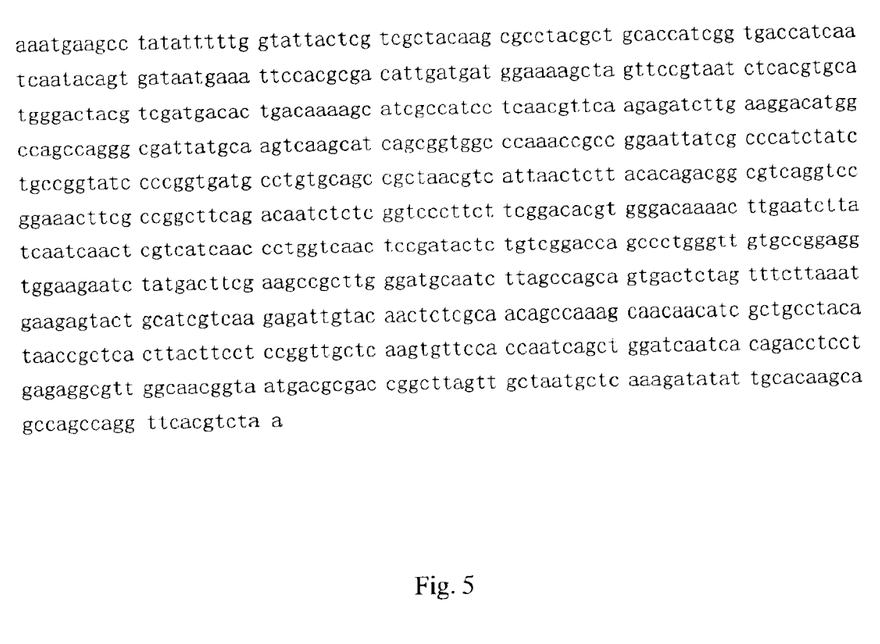
FIG. 5 shows the cDNA sequence (SEQ ID NO:1) of the fibroin L chain of *Bombyx mori*.

*Bombyx mori* mRNA was isolated from the posterior silk glands of the 5th intar larvae. A pair of PCR primers (5'-acggatccaa atgaagccta ta-3' (SEQ ID NO:7), 5'-ggctgcagtt agacgtgaac ctgg-3' (SEQ ID NO:8)) was designed base on the sequence of L-chain. The cDNA of L-chain (about 0.7 Kb), which contains signal sequence, was obtained by RT-PCR amplification from the mRNA (shown in FIG. 5).

Figure 6:
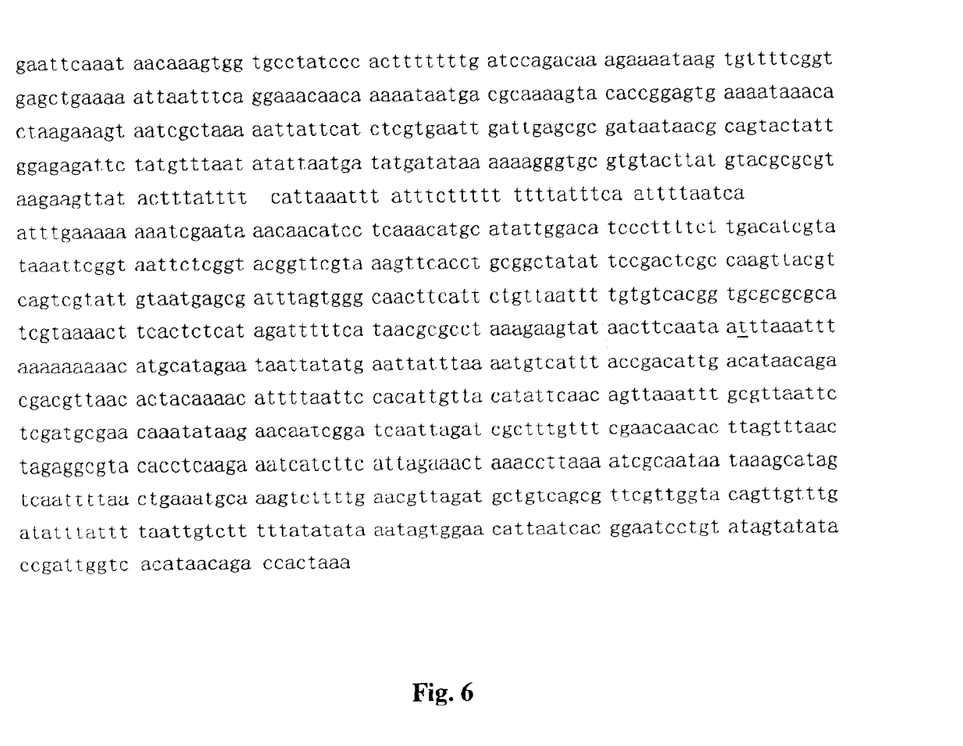
FIG. 6 shows the 5' terminal and promoter sequence (SEQ ID NO:2) of L chain gene.
Figure 7:
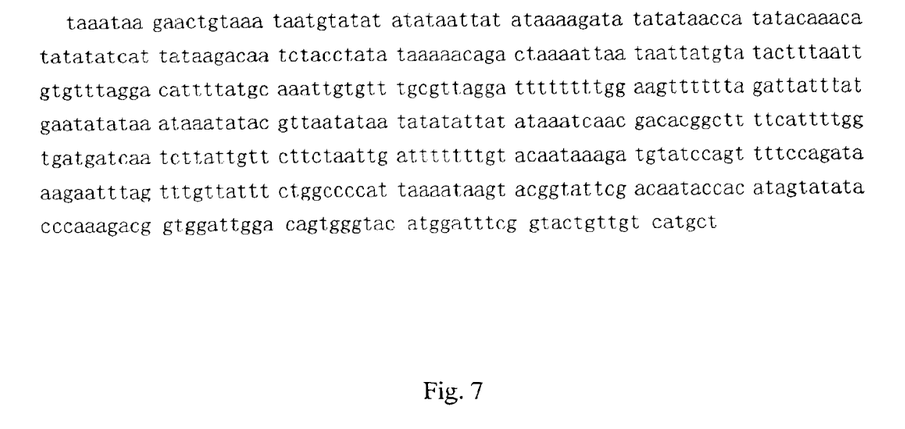
FIG. 7 shows the terminator sequence (SEQ ID NO:3) of L chain gene.

Total DNA was isolated from Bombyx mori. Based on the sequence of Light-chain gene promoter, a pair of primers was designed (5'-gagctcgaat tcaaataaca aagtggtgc-3' (SEQ ID NO:9), 5'-ctctagatta gtggtctgtt atg-3' (SEQ ID NO:10)). The 5' terminal and promoter of L-chain gene was obtained by PCR amplification (the sequence of which is shown in FIG. 6). The terminator at the 3' end was obtained in a similar manner (the sequence of which is shown in FIG. 7).

The mRNA of the major ampullate gland of *Nephila clavipes* was extracted. A pair of primers (5'-gcagcagcag cagctggagg-3' (SEQ ID NO:11), 5'-cgatgctgga agaacctaag-3' (SEQ ID NO:12)) were used to amplify a part of the repetitive nucleotide DNA sequence of the MaSP1 gene for spider dragline silk by RT-PCR. The sequence of the amplified product is shown FIG. 8.

The amplified fragments obtained above were ligated to form a fusion gene with correct reading frame. Firstly, the sequence of MaSP1 gene cDNA was inserted into the exon 7 of the L-chain cDNA to form a fusion with correct coding frame. Then the promoter and terminator of L chain were added to the fusion at the 5' and 3' terminal, respectively, to form a complete fusion gene expression unit.

Example 2
Construction of the Constitutive Gene-delivering Vector

Figure 9:
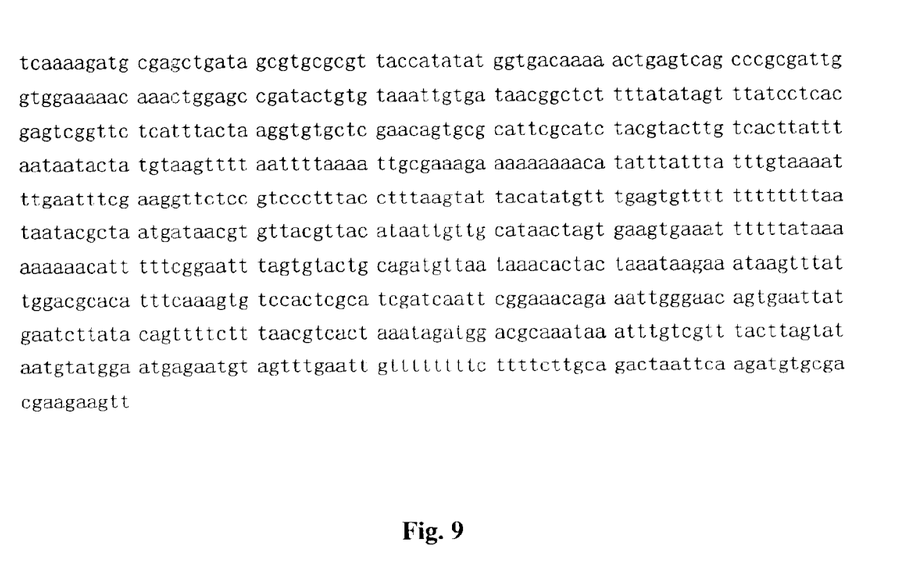
FIG. 9 shows the A3 promoter sequence (SEQ ID NO:5)

The A3promoter was firstly cloned by PCR from the total genomic DNA of *Bombyx mori* like L chain promoter, and then was added to the upstream of GFP coding sequence. A SV40 terminal polyA signal sequence was also added to th GEP gene to establish a reporter unit. Then the fusion gene expression unit and the reporter unit were linked by an artificial MCS linker of 30 bp (5'-ACCGCGGTCT AGAG-GATCCC GGGCTGCAGT 3' (SEQ ID NO:13)). At last, the ligated fragment was flanked at each end with the piggyBac ITRs (5'-CGCCGCGGCC CTAGAAAGAT AGTCT-GCGTA AAATTGACGC ATGCTGCAGT G-3' (SEQ ID NO:14)), and the product was cloned into plasmid pBS to construct th gene-delivering vector of the bi-vector transgeneic system. The sequence of A3 promoter was shown in FIG. 9.

Example 3
Construction of the Helper Vector

Figure 10:
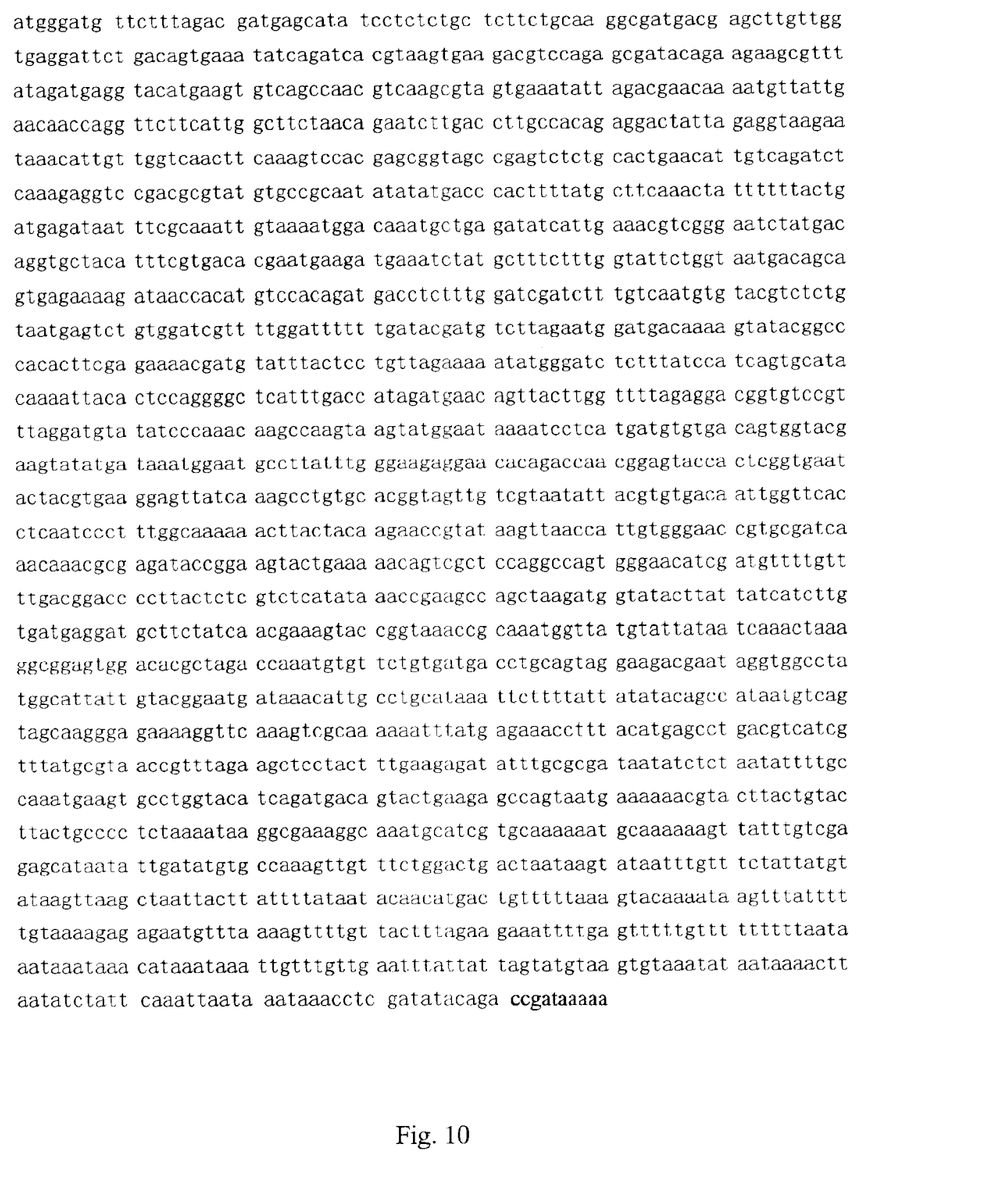
FIG. 10 shows the nucleotide sequence (SEQ ID NO:6) of transposase of piggyBac transposon.

The coding region of piggyBac transposase was cloned by PCR amplification, and then an A3 promoter and a SV40 terminator were added. The product thus obtained was ligated into plasmid pUC18 to form the helper vector. These two vectors, the constitutive gene-delivering vector obtained in Example 2 and the helper vector obtained in this Example, constitute the bi-vector transgeneic system for *Bombyx mori*. The system ensured the integration of extraneous gene into the genomic DNA of *Bombyx mori* with high efficiency and with several copies. The nucleotide sequence of transposase is shown in FIG. 10.

Example 4
Transformation and Screening of the Transgenic *Bombyx Mori*

Transformation of the silkworm eggs. The gene delivering vector and the helper vector of the transgeneic system mentioned above were introduced into the silkworm eggs by micro-injection. The embryos were incubated at 25° C. and the developing larva were raised normally.

Figure 3:
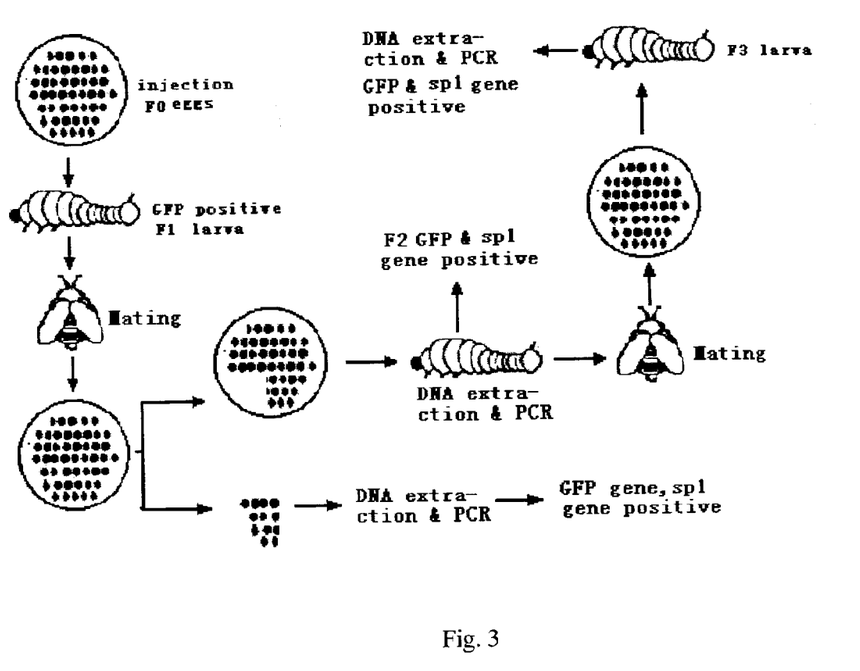
FIG. 3 shows the process for the screening of the transgenic silkworm.
Figure 4:
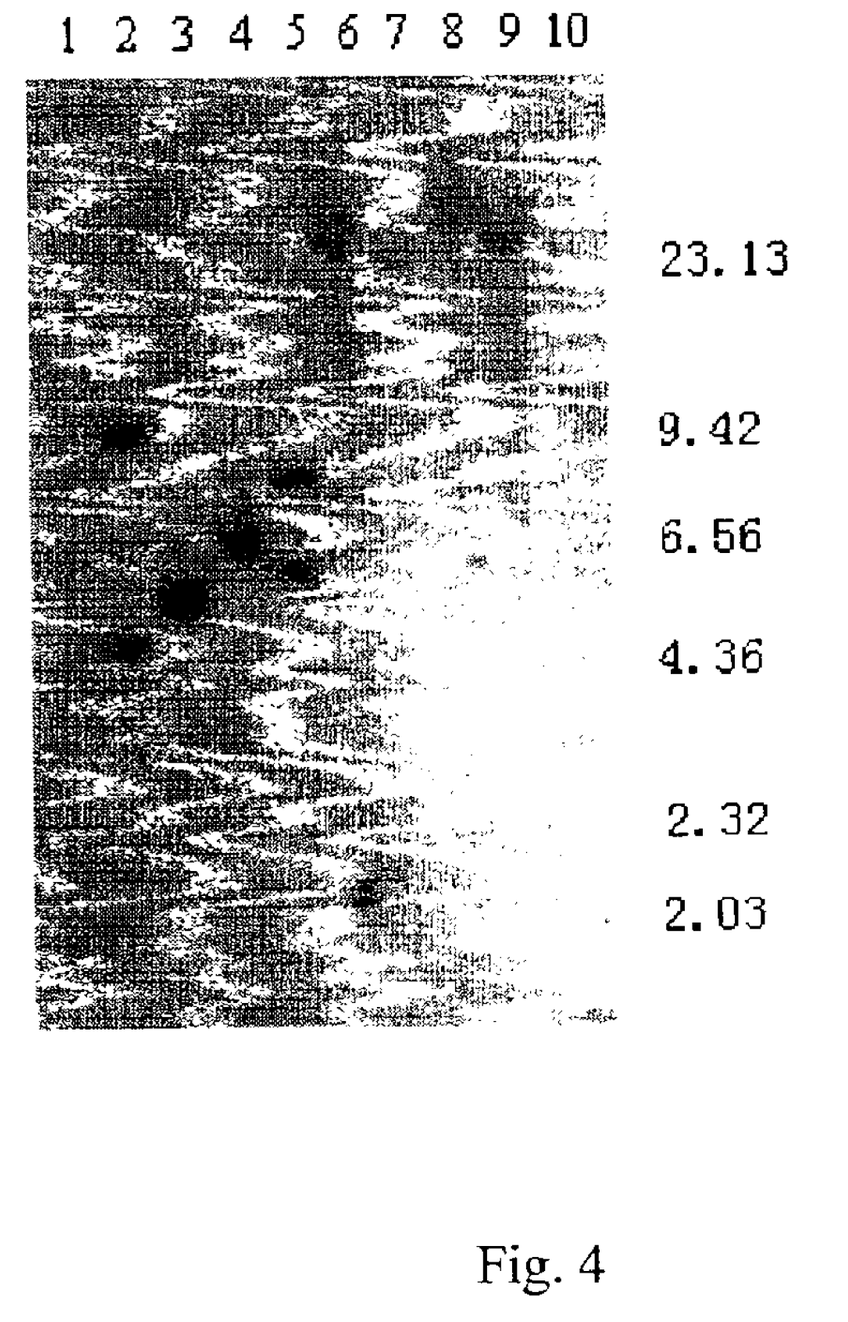
FIG. 4 shows the Southern blot analysis of the genomic DNA of the transgeneic silkworm.

Screening and characterization of transgeneic silkworm (FIG. 3). The larvae at the 2nd day of fifth instar were used for characterization, and the GFP positive larvae under UV detection of long wavelength were labeled for further characterization. In the experiment, 2000 eggs were injected, and 795 larvae and 420 progenitive month were obtained. 0.7% of the $G_0$ larvae displayed GFP fluorescence, and the putative transgenic silkworm larvae were incubated further, and sibling mated or backcrossed. The resulting eggs were divided into two parts, one was used for extraction of total DNA, and characterized by PCR. If the result was negative, the other part was discarded. Otherwise, the other part was used for further development. The developed fifth instar larvae were used for fluorescence detection again. Positive larvae were used for extracting total DNA, and characterized by PCR. Finally, the positive ones were further characterized by Southern blot analysis (FIG. 4 shows the result of southern blot using the spider dragline silk gene as a probe). The positive larvae were allowed to develop and were screened until G3, the positive ones are the transgenic Bombyx mori. Protein from posterior silk glands and cocoon of the transgenic *Bombyx mori* were extracted, and used for SDS-PAGE analysis. The result showed that the fused spider dragline silk gene product account for 30% of the total silk proteins.

We claim:

1. A method for establishing an expression system of spider dragline silk gene in *Bombyx mori*, comprising the steps of:

(1) ligating a cDNA encoding spider dragline silk protein or a cDNA encoding the repetitive amino acid sequence part of a spider dragline silk protein with a cDNA comprising the nucleotide sequence of SEQ ID NO:1 encoding the silkworm fibroin L chain, placing the ligated DNA under the control of the promoter of a L chain gene and terminating the ligated DNA with the terminator of the L chain gene, thereby obtaining a fused gene;

(2) ligating the fused gene with a reporter gene to obtain a ligated product, inserting the ligated product thus obtained between the two inverted terminal repeats of the transposon of piggyBac, thereby obtaining a recombinant transposon;

(3) constructing a transposase gene expression vector by using a transposase gene;

(4) co-transforming a silkworm egg by using the recombinant transposon obtained in step (2) and the transposase gene expression vector obtained in step (3) to obtain a transformed silkworm egg;

(5) obtaining a transgenic silkworm which expresses a spider dragline/L chain fibroin silk fusion protein by cultivating and screening the larva of a plurality of the transformed egg of step (4) for expression of the spider dragline/L chain fibroin silk fusion protein.

2. A method according to claim 1, wherein the cDNA encoding spider dragline silk protein or the cDNA encoding the repetitive amino acid sequence part of the spider dragline silk protein was fused with its 5' end to the 3' end of the cDNA comprising the nucleotide sequence of SEQ ID NO:1 encoding the silkworm fibroin L-chain.

3. A method according to claim 1, wherein the reporter gene is GFP gene.

4. A method according to claim 1, wherein the fused gene and the reporter gene in step (2) are ligated by a polynucleotide linker with the sequence
5'-ACCGCGGTCTAGAGGATCCCGGGCTGCAGT-3' (SEQ ID NO:13).

5. A method according to claim 1, wherein, in the transposase gene expression vector in step (3), a promoter A3 of the silkworm cytoplasmic alactin gene and a polyA signal sequence of SV40 are used to regulate expression of the transposase.

6. A method according to claim 1, wherein the transposase expression vector in step (3) is derived from plasmid pUC18.

7. The method of claim 2, wherein the cDNA comprising the nucleotide sequence of SEQ ID NO:4 and encoding the repetitive amino acid sequence part of the spider dragline protein is ligated to the cDNA comprising the nucleotide sequence of SEQ ID NO:1 and encoding the silkworm fibroin L chain.

8. The method of claim 1, wherein the cDNA of the *Nephila clavipes* MaSP1 gene encoding spider dragline silk protein is ligated to the cDNA comprising the nucleotide sequence of SEQ ID NO:1 and encoding the silkworm fibroin L chain.

* * * * *